(12) United States Patent
Maeshima et al.

(10) Patent No.: US 7,759,080 B2
(45) Date of Patent: Jul. 20, 2010

(54) METHOD OF DETERMINING PREGNANCY TOXEMIA

(75) Inventors: Yohei Maeshima, Okayama (JP);
Kumiko Hirokoshi, Okayama (JP);
Hirofumi Makino, Okayama (JP);
Hisashi Masuyama, Okayama (JP); Yuji Hiramatsu, Okayama (JP)

(73) Assignee: National University Corporation Okayama University, Okayama (JP)

( * ) Notice: Subject to any disclaimer, the term of this patent is extended or adjusted under 35 U.S.C. 154(b) by 39 days.

(21) Appl. No.: 11/722,840

(22) PCT Filed: Dec. 26, 2005

(86) PCT No.: PCT/JP2005/023767

§ 371 (c)(1),
(2), (4) Date: Mar. 19, 2008

(87) PCT Pub. No.: WO2006/070734

PCT Pub. Date: Jul. 6, 2006

(65) Prior Publication Data

US 2009/0111130 A1 Apr. 30, 2009

(30) Foreign Application Priority Data

Dec. 27, 2004 (JP) .............................. 2004-376343

(51) Int. Cl.
*G01N 33/53* (2006.01)
*C12Q 1/00* (2006.01)
(52) U.S. Cl. .......................................... 435/7.92; 435/4
(58) Field of Classification Search .................. 435/7.92, 435/4
See application file for complete search history.

(56) References Cited

U.S. PATENT DOCUMENTS

2003/0124129 A1 7/2003 Oliner
2005/0255114 A1 11/2005 Labat et al.

FOREIGN PATENT DOCUMENTS

JP 10-239311 9/1998

OTHER PUBLICATIONS

Loukovaara et al. Diabetic Medicine 21(7):697-704, Jul. 2004.*
Zhang er al. Molecular Medicine 7(9):624-635, 2001.*
Gonaxalez et al. Ginecol Obstet Mex 68:357-62, 2000. Abstract only.*
Shibuya, M., "Neovascularization Control by VEGF Signal", 2004,*Seikagaku*, vol. 76, No. 12, pp. 1534-1542, Yes, Abstract only.
Hirokoshi, K., et al., "Investigation of Concentration Change of the Serum Angiopoietin2 Concentration (Serum Ang-2 Concentration) in Pregnancy Toxemia", 2005, *The Japan Journal of Nephrology*, vol. 47, No. 3, p. 262, Yes, Abstract only.
Yamamoto, Y., et al. "Tumstatin Peptide, an Inhibitor of Angiogenesis, Prevents Glomerular Hypertrophy in the Early Stage of Diabetic Nephropathy", 2004,*Diabetes*, vol. 53, pp. 1831-1840.
Tian, Q., et al., "Integrated Genomic and Proteomic Analyses of Gene Expression in Mammalian Cells", *Molecular and Cellular Proteomics*, vol. 3, (2004), pp. 960-969.
QUANTIKINE®, Human Angiopoietin-2 Immunoassay; Catalog No. DANG20, SANG20, PDANG20; *R&D Systems, Inc.*, MN, U.S.A.
Hirokoshi, K., et al., "Increase of Serum Angiopoletin-2 During Pregnancy Is Suppressed in Women With Preeclampsia," *American Journal of Hypertension*, 2005, pp. 1181-1188, vol. 18(9), Elsevier Science Publishers Ltd., United Kingdom.
Zhang, E.G., et al., "The Regulation and Localization of Angiopoietin-1, -2, and Their Receptor Tie2 in Normal and Pathologic Human Placentae," *Molecular Medicine*, 2001, pp. 624-635, vol. 7(9), Cambridge, MA.
Wulff, C., et al., "Angiogenesis During Primate Placentation in Health and Disease," *Reproduction*, 2003, pp. 569-577, vol. 126(5), Cambridge, England.
Smith, S.K., et al., "Angiogenic Growth Factor Expression in Placenta," *Seminars in Perinatology*, 2000, pp. 82-86, vol. 24(1), W.B. Saunders, GB.
Nadar, S., et al., "Plasma Markers of Angiogenesis in Pregnancy Induced Hypertention," *American Journal of Hypertension*, 2004, pp. S161-S162, vol. 17(5), Elsevier Science Publishers Ltd., United Kingdom.

* cited by examiner

*Primary Examiner*—Thaian N Ton
*Assistant Examiner*—Marcia S Noble
(74) *Attorney, Agent, or Firm*—Alston & Bird LLP (57) ABSTRACT

It is intended to provide a method of detecting the onset of pregnancy toxemia whereby the onset risk of pregnancy toxemia can be adequately evaluated. Namely, a method of detecting the onset of pregnancy toxemia in a pregnant mammal which comprises the measurement step of measuring the concentration of angiopoietin-2 in a body fluid, the comparison step of comparing the angiopoietin-2 concentration obtained in the above measurement step with a normal level, and the judgment step of judging the presence or absence of the onset risk of pregnancy toxemia based on the results of the above comparison step. In the judgment step, it may be considered that the patient has a risk of the onset of pregnancy toxemia in the case where the angiopoietin-2 concentration obtained in the measurement step is lower than the normal level.

5 Claims, 4 Drawing Sheets

METHOD OF DETERMINING PREGNANCY TOXEMIA

FIELD OF THE INVENTION

The present invention relates to a method of examining pregnancy toxemia, and more specifically to a method of examining the pregnancy toxemia allowing evaluating with ease and sufficient accuracy whether or not a pregnant woman currently suffers from the pregnancy toxemia, or whether or not the pregnant woman has an onset risk of the pregnancy toxemia in the future. In the present invention, a case in which a pregnant woman currently suffers from the pregnancy toxemia, and a case in which the pregnant woman has a future onset risk of pregnancy toxemia are generically referred to as "there is an onset risk of the pregnancy toxemia". The "method of examining the pregnancy toxemia" according to the present invention is a method of examining this onset risk of the pregnancy toxemia.

BACKGROUND ART

The pregnancy toxemia is one of clinically important complications appearing during the pregnancy, induces hypertension, proteinuria, edema, and the like, and has an adverse effect on the mother's body and/or neonate.

For example, a method of evaluating the amount of fat in the mother's body and associating the evaluated amount of fat with the onset risk of pregnancy toxemia is known as a method of appreciating the onset risk of pregnancy toxemia (for example, refer to Patent documents 1 and 2).

Patent document 1 discloses ultrasonic diagnostic equipment used for a periodic medical examination during the pregnancy for appreciating the "onset risk of the pregnancy toxemia by healthcare in which a change in a pregnant woman's body fat ratio or weight is associated with the growth curve of the fetus" (That is, the future onset risk of pregnancy toxemia is evaluated.).

Patent document 2 discloses the judgment of the onset of pregnancy toxemia by using "a healthcare apparatus for pregnant women comprising: input means for inputting personal data on a pregnant woman, such as height and weight, arithmetic means for calculating the amount of body water and the amount of fat by a bioelectric impedance analysis, standard setting means provided with standard values according to the week of the pregnancy, comparison means for comparing the results of operations by the arithmetic means with the standard values, and judgment means for determining a pregnant woman's health condition based on the comparison results of the comparison means (claim 1), wherein the "judgment means determines the onset of pregnancy toxemia" (claim 3) (That is, the current onset of the pregnancy toxemia is evaluated.).

[Patent Reference 1]
Japanese Unexamined Patent Application Publication No. 2002-604 (for example, Problems to be solved in Abstract)

[Patent Reference 2]
Japanese Unexamined Patent Application Publication No. 2003-33356 (for example, claims 1 and 3)

DISCLOSURE OF THE INVENTION

Problem to be Solved by the Invention

However, the inventions disclosed in these Patent documents 1 and 2 evaluate the onset risk of pregnancy toxemia from the amount of fat in the mother's body. Although a certain relationship is observed between the two, the mother's body with a large amount of fat does not always develop the pregnancy toxemia, and the mother's body with a small amount of fat is not always free from the onset of the pregnancy toxemia. Thus, there has been no method of adequately evaluating the onset risk of the pregnancy toxemia so far.

Therefore, it is an objective of the present invention to provide a method of examining the pregnancy toxemia to allow adequately evaluating the onset risk of the pregnancy toxemia.

Means for Solving Problem

The method of examining the pregnancy toxemia according to the present invention (a method of evaluating an onset risk of pregnancy toxemia, that is, a method of evaluating at least one of the current onset of the pregnancy toxemia and the future onset risk of pregnancy toxemia) is a method of examining the pregnancy toxemia (hereinafter referred to as "first present method") characterized by measuring the concentration of angiopoietin-2 in the body fluid of a pregnant mammal, and comparing the concentration of angiopoietin-2 obtained in the measurement with that at a normal level.

The first present method includes the following modes (1-1) to (1-4).

(1-1) The above-mentioned method of examining the pregnancy toxemia wherein the concentration at the normal level is 6 ng/ml.

(1-2) The above-mentioned method of examining the pregnancy toxemia wherein the body fluid is blood.

(1-3) The above-mentioned method of examining the pregnancy toxemia wherein the measurement is made for a mammal after 20 weeks of the pregnancy.

(1-4) The above-mentioned method of examining the pregnancy toxemia wherein the measurement is made by the ELISA method.

Further, the method of examining the pregnancy toxemia according to the present invention (a method of evaluating the onset risk of the pregnancy toxemia, that is, a method of evaluating at least one of the current onset of the pregnancy toxemia and the future onset risk of the pregnancy toxemia) is a method of detecting the onset of the pregnancy toxemia (hereinafter referred to as "second present method") comprising: a measurement step of measuring the concentration of angiopoietin-2 in the body fluid of a pregnant mammal, a comparison step of comparing the concentration of angiopoietin-2 obtained in the measurement step with that at a normal level, and a judgment step of determining the presence or absence of the onset risk of the pregnancy toxemia based on a result in the comparison step.

The second present method includes the following modes (2-1) to (2-4).

(2-1) The above-mentioned method of detecting the onset of the pregnancy toxemia is a method of determining that there is the onset risk of the pregnancy toxemia when the concentration of angiopoietin-2 obtained in the measurement step is lower than the concentration at the normal level in the judgment step.

(2-2) The above-mentioned method of detecting the onset of the pregnancy toxemia wherein the body fluid is blood.

(2-3) The above-mentioned method of detecting the onset of the pregnancy toxemia wherein the measurement step is a measuring step which applies to a mammal in the pregnancy of equal to or more than 20 weeks.

(2-4) The above-mentioned method of detecting the onset of the pregnancy toxemia wherein the measurement step is a step in which the ELISA method is utilized.

Further, the present invention provides a reagent for the detection of pregnancy toxemia (hereinafter referred to as "present reagent") used for detecting the onset of the pregnancy toxemia. That is, the present reagent is a reagent for the detection of the pregnancy toxemia containing a reagent for measuring the concentration of angiopoietin-2 in the body fluid.

The present reagent can be utilized for detecting the pregnancy toxemia.

BEST MODE FOR CARRYING OUT THE INVENTION

Method of Detecting Onset of Pregnancy Toxemia According to the Present Invention (Present Method)

The first present method is a method of examining pregnancy toxemia intended for a pregnant mammal, characterized by measuring a concentration of angiopoietin-2 in a body fluid, and comparing the concentration of angiopoietin-2 obtained in the measurement with a concentration at the normal level.

The second present method is a method of detecting the onset of pregnancy toxemia intended for a pregnant mammal, comprising: a measurement step of measuring a concentration of angiopoietin-2 (angiopoietin-2) in a body fluid, a comparison step of comparing the concentration of angiopoietin-2 obtained in the measurement step with a concentration at a normal level, and a judgment step of determining either presence or absence of the onset risk of the pregnancy toxemia based on a result of the comparison step.

The mammal covered by the present invention is not particularly limited as long as a difference in the concentration of angiopoietin-2 in the body fluid is rendered according to whether or not the mammal currently suffers from the pregnancy toxemia, or whether or not there is presence or absence of the future onset risk of the pregnancy toxemia. The mammal may be, for example, the human, swine, horse, bovine, sheep, goat, dog, cat, rabbit, hamster, rat, or mouse.

The body fluid may be exemplified as blood or urine in which the concentration of angiopoietin-2 is measured in the concentration measurement (measurement step) of angiopoietin-2 in the body fluid. The body fluid is preferably blood. The concentration of angiopoietin-2 in blood can be measured by utilizing serum or plasma as a measurement sample.

The gestational age of the "pregnant mammal" covered by the present method is not particularly limited as long as it is a period in which a significant difference in the angiopoietin-2 concentrations between a normal pregnant female and a sufferer of the pregnancy toxemia is rendered. In the case of measurement (measurement step) of the concentration of angiopoietin-2 in human serum (body fluid) during the pregnancy, the time of commencement is preferably after 15 weeks, more preferably after 20 weeks, and most preferably after 25 weeks, for example, and the time of termination is preferably before 40 weeks, and more preferably before 38 weeks.

When the concentration of angiopoietin-2 in the body fluid is measured (measurement step) at an early stage, in particular after 20 weeks (for example, after 20 weeks and before 25 weeks, after 20 weeks and before 30 weeks, or the like), the onset of the pregnancy toxemia can be found at the early stage, or the future onset risk of the pregnancy toxemia can be recognized at the early stage. Therefore, the pregnancy toxemia can be treated at the early stage (for example, cautions in a daily life, instructions, visitation to a medical institution, and the like), which may be useful for preventing the symptom from becoming severer such that the improvement of prognosis may also be achieved.

The concentration of angiopoietin-2 in the body fluid of a pregnant female that does not currently suffering from the pregnancy toxemia and will not suffer from the pregnancy toxemia in the future (having no medical histories such as a renal disease and essential hypertension) may be adopted as the concentration at the normal level (the concentration at the normal level in the comparison step) with which the concentration of angiopoietin-2 obtained in the measurement (the measurement step) is compared. For example, the concentration of angiopoietin-2 in the serum (body fluid) of the woman during the pregnancy who is not currently suffering from the pregnancy toxemia and will not suffer from the pregnancy toxemia in the future is approximately 8.0 ng/ml to 30.0 ng/ml (an example of the concentration in the normal pregnancy).

In addition, the pregnancy toxemia is described in "Information to members: Definition and classification of pregnancy-induced hypertension syndrome", Jpn, J. Obst. Gyn., p.p. 3-4, Vol. 56, No. 9 (Sep. 16, 2004), published by Japan Society of Obstetrics and Gynecology (Chairman: Shingo Fujii) on Aug. 9, 2004. Specifically, it refers to either a case in which hypertension is observed in a period from 20 weeks of pregnancy to 12 weeks post partum or a case in which proteinuria accompanies the hypertension, as long as both of the foregoing cases are not induced by accidental complications. Generally, the pregnancy toxemia is divided into a slight illness and a serious illness, and the definitions of these slight illness and serious illness are as follows, respectively.

1. Slight Illness:

(1) Hypertension: a case in which blood pressure corresponds to either the following (a) or (b):

(a) Systolic pressure is 140 mmHg or more and less than 160 mmHg.

(b) Diastolic pressure is 90 mmHg or more and less than 110 mmHg.

(2) Proteinuria:

It is basically determined by the determination method with 24-hour urine. A case in which it is 300 mg/day or more and less than 2 g/day.

2. Serious Illness:

(1) Hypertension: a case in which blood pressure corresponds to either the following (c) or (d):
  (c) Systolic pressure is 160 mmHg or more.
  (d) Diastolic pressure is 110 mmHg or more.

(2) Proteinuria:

It is basically determined by the determination method with 24-hour urine. A case in which it is 2 g/day or more. A case in which it is consecutively 3+(300 mg/dl) or more in a plurality of fresh urine analyses when casual urine is used.

The "method of examining pregnancy toxemia" according to the present invention is utilized for at least either detecting the current onset of the pregnancy toxemia or the future onset risk of the pregnancy toxemia (Needless to say that it may be utilized for both cases.).

Determining either presence or absence of the onset risk of the pregnancy toxemia (judgment step) based on the result of the comparison of the concentration of angiopoietin-2 obtained in the measurement with that at the normal level (comparison step) is not limited in any way as long as the (current) onset of the pregnancy toxemia or the future onset risk is determined based on the comparison result. For example, in the case of determining either presence or absence of the (current) onset of the pregnancy toxemia, the (current) onset of the pregnancy toxemia is determined to be present when the concentration of angiopoietin-2 in the body fluid indicates the pregnancy toxemia while clinical data (the amount of urinary protein which is the representative clinical data of the pregnancy toxemia, or the like) suggests the onset of the pregnancy toxemia. Further, for example, in the case of determining the future onset risk of the pregnancy toxemia, the future onset risk of the pregnancy toxemia is determined to exist when the concentration of angiopoietin-2 in the body fluid indicates the pregnancy toxemia while clinical data (the amount of urinary protein which is the representative clinical data of pregnancy toxemia, or the like) does not suggest the onset of pregnancy toxemia.

Further, according to the research results by the present inventors, the concentration of angiopoietin-2 in the body fluids of a pregnant female that was currently suffering from the pregnancy toxemia or would suffer from the pregnancy toxemia in the future, was lower than the concentration of angiopoietin-2 in the body fluid of a pregnant female that was not currently suffering from the pregnancy toxemia and would not suffer from the pregnancy toxemia in the future. For this reason, in determining either presence or absence of the onset risk of the pregnancy toxemia (judgment step) based on the result of the comparison (comparison step) of the concentration of angiopoietin-2 obtained in the measurement with the concentration at the normal level, the determination of the current or future onset of the pregnancy toxemia may be made when the concentration of angiopoietin-2 obtained in the measurement (measurement step) is lower than the concentration at the normal level.

The method of measuring the concentration of angiopoietin-2 in the body fluid (measurement step) is not limited in any way, and any method may be adopted as long as the method allows measuring the concentration of angiopoietin-2 in the body fluid. For example, the ELISA method (Enzyme-Linked Immunosorbent Assay), the Western blot technique, the radioimmunoassay (RIA) method, or the like may be used.

Above all, when the ELISA method is used, the measurement can be easily made based on commercially-available measurement kits, procedures therefor, and the like. It is possible to conduct a quantitative evaluation without requiring the handling of radioactive substances, and only a small amount of sample is required (approximately 200 microliter, for example, when the concentration of angiopoietin-2 in serum is measured). Thus, the ELISA method has advantages.

(Reagent for Detection of Pregnancy Toxemia According to the Present Invention (Present Reagent))

The present reagent is a reagent for the detection of the pregnancy toxemia including a reagent for measuring the concentration of angiopoietin-2 in the body fluid.

As the reagent (including also a reagent in which a plurality of kinds of reagents are combined) for measuring the concentration of angiopoietin-2 in the body fluid, any reagent may be adopted without being limited hereto in any way as long as the reagent allows to measure the concentration of angiopoietin-2 in the body fluid. The reagent may be a reagent (or the combination of reagents) for conducting any one of the ELISA method (Enzyme-Linked Immunosorbent Assay), the Western blot technique, the radioimmunoassay (RIA: Radioimmunoassay) method, and the like utilized for the method for measuring the concentration of angiopoietin-2 in the body fluid (measurement step) according to the present method as mentioned above.

For example, when the concentration of angiopoietin-2 in the body fluid is measured according to the ELISA method, the present reagent may contain a reagent of a mouse monoclonal anti-angiopoietin-2 antibody, recombinant human-derived angiopoietin-2, and a horseradish peroxidase-labeled mouse monoclonal anti-angiopoietin-2 antibody. In addition, "Quantikine human Angiopoietin-2 kit" (trademark) of R&D Systems contains such reagents and is commercially available.

The present reagent of the kind can be utilized for performing the measurement step of the present method, and it can be provided for detecting the pregnancy toxemia in accordance with the present method (It is utilized to determine whether either presence or absence of the current onset of the pregnancy toxemia or to evaluate the future onset risk of the pregnancy toxemia.).

Examples

In the following, the present invention is described in more detail based on examples. However, the present invention is not limited to these examples.

(1) Subjects

The following experiments were conducted for 29 healthy pregnant women (normal pregnancy group (healthy group)), 26 pregnancy toxemia patients (toxemia group), 20 healthy non-pregnant women (non-pregnancy group), and 11 women within one week post partum (2 cases of pregnancy toxemia, and 9 cases of healthy group) (group within one week post partum). All these subjects are Japanese women aged from 17 to 41 without a medical history of disease such as a renal disease or essential hypertension. The healthy pregnant women and the pregnancy toxemia patients were in 25 to 40 weeks of gestational age.

In addition, the pregnant women whose systolic pressure was 140 mmHg or more, diastolic pressure was 90 mmHg or more, and the amount of urinary protein during 24-hour urine collection was 300 mg/day or more were defined as women suffering from the pregnancy toxemia and pregnant women who did not satisfy the definition were defined as healthy pregnant women.

(2) Preparation of Serum Sample

Blood was obtained from above each subject (among the normal pregnancy group, the toxemia group, the non-pregnancy group, and the group within one week post partum), and serum was prepared in accordance with the conventional method. As for the pregnancy toxemia patients (among the toxemia group), blood obtained immediately after the onset of pregnancy toxemia was used. The prepared serum was stored at −80 degrees C. before use and dissolved under a normal room temperature at the time of use.

(3) Measurement of Serum Angiopoietin-2 Concentration

The angiopoietin-2 concentration (serum Ang-2 concentration) was measured in the serum sample of each subject (among the normal pregnancy group, the toxemia group, the non-pregnancy group, and the group within one week post partum) prepared as described above. The measurement of the serum Ang-2 concentration was made by using an ELISA kit ("Quantikine Human Angiopoietin-2 kit" (trademark)) (hereinafter referred to as "utilized kit") of R&D Systems and in accordance with the manual thereof.

The above ELISA kit (utilized kit) includes the following reagents and the like.

(a) "Angiopoietin-2 Microplate": a polystyrene microtiter tray having 96 wells coated with a mouse monoclonal antibody for angiopoietin-2.

(b) "Angiopoietin-2 Conjugate": a reagent containing a mouse monoclonal antibody for angiopoietin-2 combined with horseradish peroxidase (containing a preservative).

(c) "Angiopoietin-2 standard": a reagent (30 ng/ml) containing recombinant human-derived angiopoietin-2 which is a specimen in buffer protein (containing a preservative).

(d) "Assay Diluent RD1-76": a diluted solution for measurement containing blue dye and buffer protein (containing a preservative).

(e) "Calibrator Diluent RD5-5": a diluted solution containing buffer protein (containing a preservative).

(f) "Wash buffer concentrate": a 25 time concentrated solution of a buffering surfactant (containing a preservative).

(g) "Color Reagent A": stabilized hydrogen peroxide.

(h) "Color Reagent B": stabilized chromogen (tetramethyl benzidine)

(i) "Stop Solution": 2N sulfuric acid.

(j) "Plate Covers": plate covers.

(3-1) Measurement of Serum Angiopoietin-2 Concentration

The serum angiopoietin-2 concentration (serum Ang-2 concentration) was measured in accordance with the following steps.

1. "Assay Diluent RD1-76" was added to each well of the "Angiopoietin-2 Microplate" by 100 µl.

2. The serum sample (among the normal pregnancy group, the toxemia group, the non-pregnancy group, the group within one week post partum) or the standard solution of angiopoietin-2 was added to each well by 50 µl. Then the plate was covered with the "Plate Covers", and a reaction was caused for 2 hours while shaking the plate horizontally at a room temperature (500 rpm±50 rpm). The serum sample was diluted 5 times by using "Calibrator Diluent RD5-5" before use. Eight kinds of dilution series (0 pg/ml, 46.9 pg/ml, 93.7 pg/ml, 187.5 pg/ml, 375 pg/ml, 750 pg/ml, 1500 pg/ml, and 3000 pg/ml) prepared by diluting "Angiopoietin-2 standard" (30 ng/ml) with "Calibrator Diluent RD 5-5" were used as the standard solution of angiopoietin-2.

3. After reaction, the resultant reaction solution was sucked and removed from each well, and each well was washed with a cleaning liquid (400 µl/well). This operation was repeated 3 times. The cleaning liquid was obtained by diluting "Wash buffer concentrate" (×25 concentrated solution) 25 times with deionized water or distilled water. After washing, the cleaning liquid was removed thoroughly from each well, and moisture was removed with a paper towel.

4. Then, 200 µl of "Angiopoietin-2 Conjugate" was added to each well. The plate was covered with "Plate Covers", and a reaction was caused for 2 hours while shaking the plate horizontally at the room temperature (500 rpm±50 rpm).

5. After reaction, each well was washed similar to the operation of the above item 3.

6. After washing, 200 µl of substrate solution was added to each well, and reacted for 30 minutes at the room temperature while shielding each well from light. The substrate solution was prepared by mixing "Color Reagent A" and "Color Reagent B" of the same amount (The substrate solution was used within 15 minutes after mixing.).

7. After reaction, 50 µl of "Stop Solution" was added to each well.

8. Within 30 minutes after the addition of "Stop Solution", the absorbancy of the resultant reaction solution of each well was measured at a wavelength of 450 nm, and absorbancy at a wavelength of 540 nm or 570 nm was deducted from the measured value. Here, an absorption spectrophotometer (measurement plate reader) with "Model 550 microplate reader" (trademark) made by BIO-RAD Laboratories was used for measuring the absorbancy. Measurements were made using dual wavelengths (450 nm and 570 nm) while switching on a shaker.

A calibration curve was prepared based on results obtained from the standard solution of angiopoietin-2, and the angiopoietin-2 concentration of each subject's serum sample (among the normal pregnancy group, the toxemia group, the non-pregnancy group, the group within one week post partum) was determined using the calibration curve. Two specimens of each sample were measured (duplicated), and a statistical analysis (Software "StatView" (trademark) made by Abacus Concepts was used.) was conducted based on each mean value. The minimum mean detection concentration of angiopoietin-2 is 8.29 ng/ml, and common coefficient deviations between assays and in the assay were 6.9% and 10.4% or less, respectively.

(3-2) Measurement Results of Serum Angiopoietin-2 Concentrations

Figure 1:
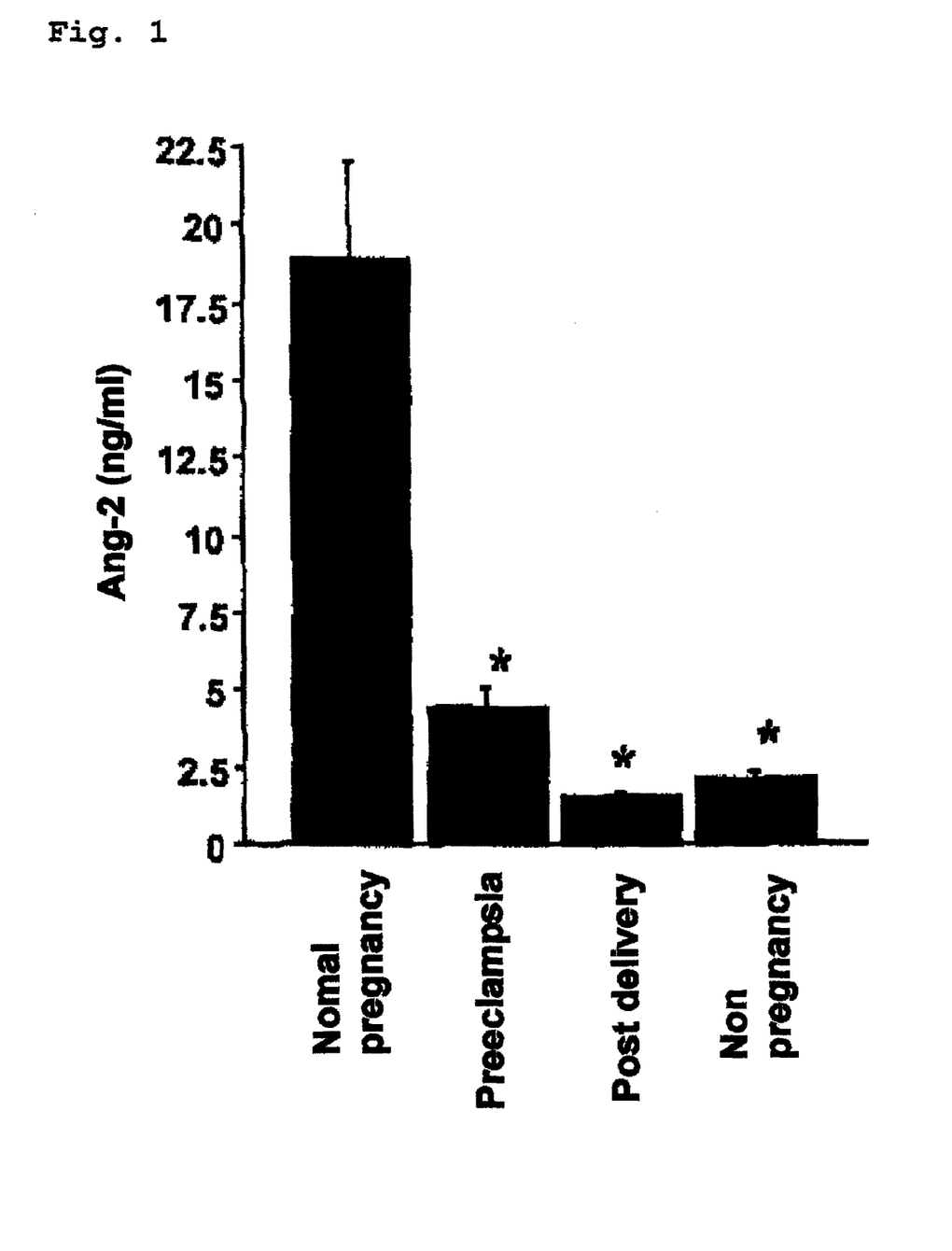
FIG. 1 is a graph showing the angiopoietin-2 concentration (serum Ang-2 concentration) of each subject's serum sample (normal pregnancy group, toxemia group (preeclampsia), non-pregnancy group, group within one week post partum (post delivery)).

FIG. 1 shows the angiopoietin-2 concentration (serum Ang-2 concentration) of each subject's serum sample (among the normal pregnancy group, the toxemia group, the non-pregnancy group, the group within one week post partum) obtained from the above results. In FIG. 1, the vertical axis represents the angiopoietin-2 concentration (unit: ng/ml) in serum. In FIG. 1, "Normal pregnancy" indicates the normal pregnancy group (healthy group) in FIG. 1, "Preeclampsia" indicates the toxemia group in FIG. 1, "Post delivery" indicates the group within one week post partum in FIG. 1, and "Non-pregnancy" indicates the non-pregnancy group in FIG. 1.

As seen in FIG. 1, the serum Ang-2 concentrations of the normal pregnancy group (Normal pregnancy) were 18.9±3.2 ng/ml, and significantly higher as compared with the serum Ang-2 concentrations (2.1±0.2 ng/ml) of the non-pregnancy group (Non-pregnancy). On the other hand, the serum Ang-2 concentrations of the toxemia group (Preeclampsia) were 4.5±0.6 ng/ml, and remarkably low as compared with the serum Ang-2 concentrations (18.9±3.2 ng/ml, p<0.0001) of the normal pregnancy group (Normal pregnancy). The serum Ang-2 concentrations of the group within one week post partum (Post delivery) showed low values to the same extent as in the non-pregnancy group regardless of the normal pregnancy and the pregnancy toxemia.

(4) Measurement of Serum Creatinine, Creatinine Clearance, and Amount of Daily Urinary Protein The serum creatinine and the creatinine clearance of the serum sample of each subject (among the normal pregnancy group, the toxemia group, the non-pregnancy group, and the group within one week post partum) prepared as described above were measured in accordance with the conventional method. Daily urine was obtained (24-hour urine collection) from each subject, and a daily amount of protein was measured in accordance with the conventional method. Two specimens of each sample were measured (duplicated), a statistical analysis (Software "StatView" (trademark) made by Abacus Concepts was used.) is conducted based on each mean value.

A method of measuring the serum creatinine, the creatinine clearance, and the amount of daily urinary protein may be based on, for example, "Tumstatin peptide, an inhibitor of angiogenesis, prevents glomerular hypertrophy in the early stage of diabetic nephropathy", presented by Yamamoto, Y., Maeshima, Y., Kitayama, H., Kitamura, S., Takazawa, Y., Sugiyama, H., Yamasaki, Y., and Makino, H. in Diabetes, Vol. 53, p.p. 1831-1840, 2004.

Table 1 shows the results. All values are indicated with a mean value±a standard error. The unit of creatinine clearance is ml/min, and the unit of amount of daily urinary protein is g/day.

stage, and the Scheffe's method in the second stage.) to conduct comparative examination in the group between the clinical parameters (specifically age, pregnancy period (gestational age), mean blood pressure, serum creatinine, creatinine clearance, and daily urinary protein determination) shown in Table 1 and the serum angiopoietin-2 concentrations. Software "StatView" (trademark) made by Abacus Concepts was used for statistical analysis, and a correlation between two groups was calculated using the Spearman's test. The serum angiopoietin-2 concentrations of the toxemia group were lower as compared with the serum angiopoietin-2 concentrations of the normal pregnancy group (healthy group), which was statistically judged to be significant with $p<0.05$.

Figure 2:
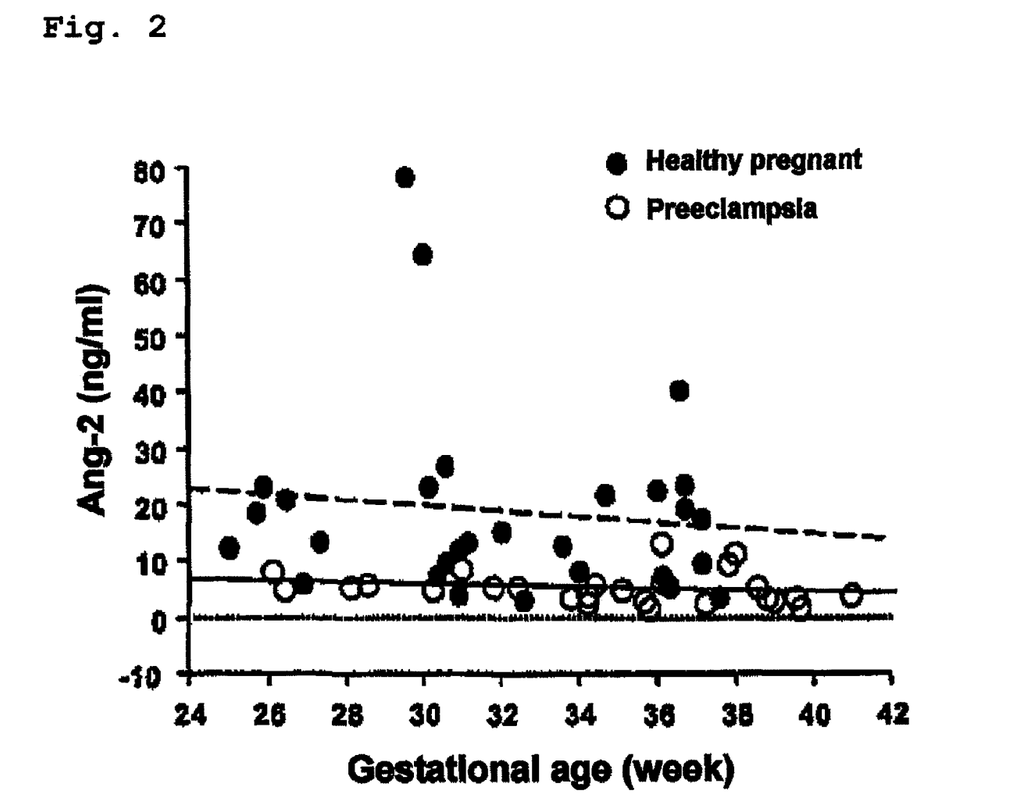
FIG. 2 is a graph showing a relationship between the serum angiopoietin-2 concentration (serum Ang-2 concentration) of the normal pregnancy group (black circle) and the toxemia group (white circle), and gestational age (week).
Figure 3:
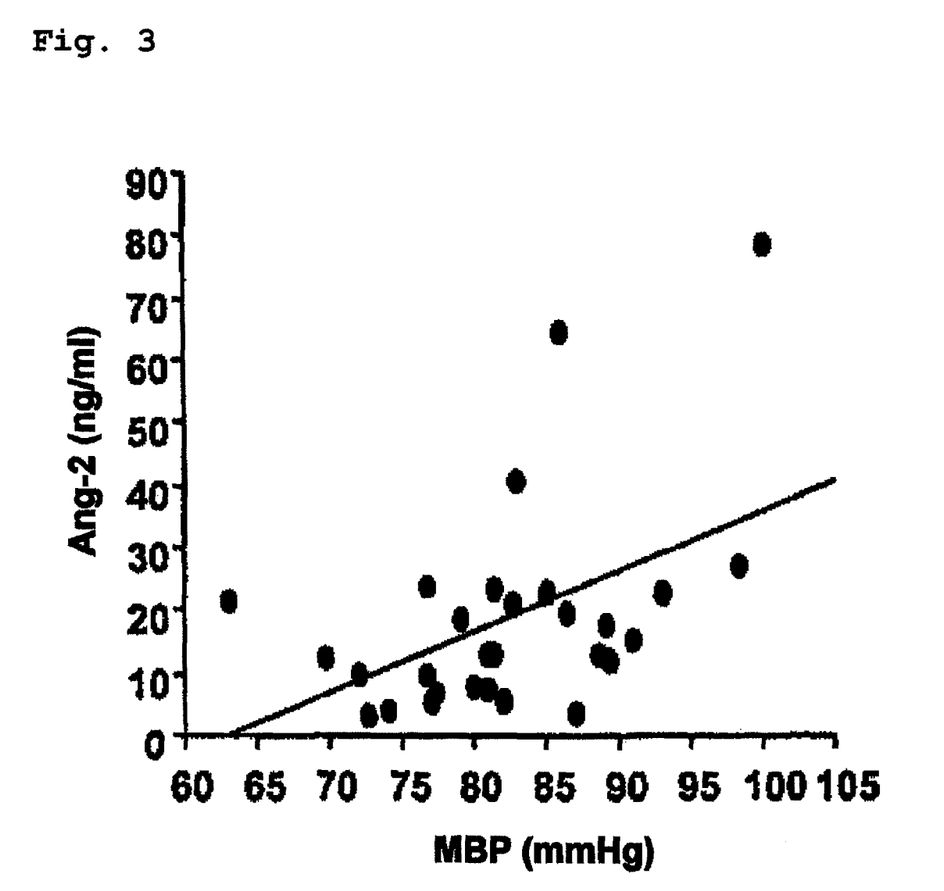
FIG. 3 is a graph showing a relationship between the mean blood pressure and the serum angiopoietin-2 concentration (serum Ang-2 concentration) of the normal pregnancy group.
Figure 4:
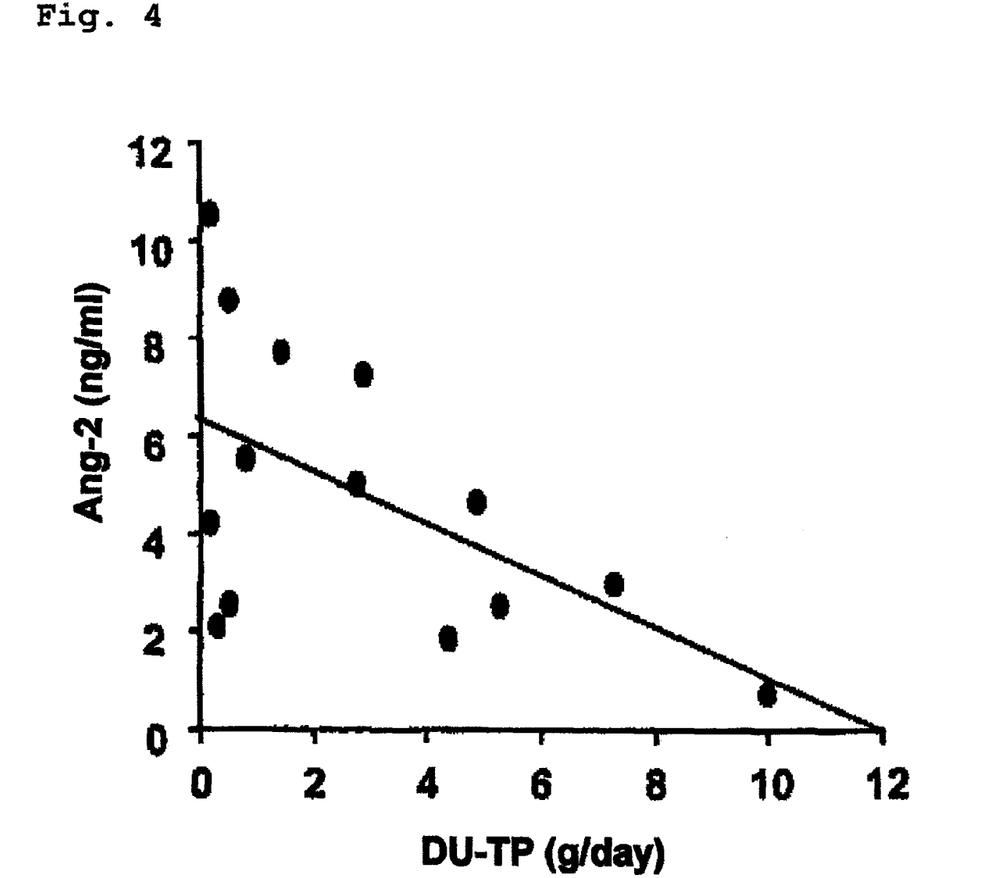
FIG. 4 is a graph showing a relationship between the amount of daily urinary protein and the serum angiopoietin-2 concentration (serum Ang-2 concentration) of the toxemia group.

FIG. 2 shows a relationship between the serum angiopoietin-2 concentrations (serum Ang-2 concentrations) and the gestational age (week) in the normal pregnancy group and the toxemia group. FIG. 3 shows a relationship between the serum Ang-2 concentrations and the mean blood pressure in the normal pregnancy group. FIG. 4 shows a relationship between the serum Ang-2 concentrations and the amount of daily urinary protein in the toxemia group.

FIG. 2 is a graph in which the horizontal axis represents the gestational age (unit: week), and the vertical axis represents the serum angiopoietin-2 concentration (serum Ang-2 concentration, unit: ng/ml). As seen in FIG. 2, no significant correlation was observed between the serum Ang-2 concentrations of the normal pregnancy group (black circle: "Healthy pregnant") and the toxemia group (white circle: "Preeclampsia") and the gestational age, but the serum Ang-2 concentrations had a tendency to decrease as the gestational age progressed.

FIG. 3 is a graph in which the horizontal axis represents the mean blood pressure (MBP, unit: mmHg), and the vertical axis represents the serum angiopoietin-2 concentration (serum Ang-2 concentration, unit: ng/ml). As seen in FIG. 3, the mean blood pressure of the normal pregnancy group showed a significant positive correlation with the serum Ang-2 con-

TABLE 1

| Group | Normal pregnancy group (Healthy group) | Toxemia group | Non-pregnancy group |
|---|---|---|---|
| Number of subjects (n) | 29 | 26 | 20 |
| Mean age | 30.5 ± 5.8 | 31.0 ± 4.5 | 32.9 ± 4.4 |
| Gestational age (week) | 32.0 ± 4.0 | 34.5 ± 4.2 | |
| Mean blood pressure (mmHg) | 82.2 ± 8.2 | 106.6 ± 15.6 (*) | N.D. |
| Serum creatinine (mg/dl) | N.D. | 0.63 ± 0.19 | N.D. |
| Creatinine clearance (ml/min) | N.D. | 91.9 ± 29.1 | N.D. |
| Daily urinary protein (g/day) | N.D. | 2.79 ± 2.81 | N.D. |

(*) $P < 0.02$ vs. Healthy group
N.D.: No applicable data

As shown in Table 1, the mean blood pressure of the toxemia group indicated significantly higher values than the mean blood pressure of the normal pregnancy group. As for the toxemia group, the values of the serum creatinine and the creatinine clearance, which are the parameters of renal functions, were within the normal range, but the amount of daily urinary protein was as high as approximately 3 g.

(5) Correlation Between Serum Angiopoietin-2 Concentration and Clinical Parameters (Gestational Age, Mean Blood Pressure, Serum Creatinine, Creatinine Clearance, and Amount of Daily Urinary Protein)

The method of Kruskal-Wallice (Kruskal-Wallice test) and the Scheffe's method (Scheffe's test) are used (Analyses were conducted using the method of Kruskal-Wallice in the first centration ($r=0.469$, $p=0.0095$), but no correlation was observed in the toxemia group.

FIG. 4 is a graph in which the horizontal axis represents the amount of daily urinary protein (DU-TP, unit: g/day), and the vertical axis the serum angiopoietin-2 concentration (serum Ang-2 concentration, unit: ng/ml). As shown in FIG. 4, the amount of daily urinary protein of the toxemia group showed a significant negative correlation with the serum Ang-2 concentration ($r=0.55$, $p=0.0401$). As for the toxemia group, no correlation was observed between the renal function parameters (serum creatinine and creatinine clearance) and the serum Ang-2 concentration.

(6) Discussion

As described above, the serum Ang-2 concentrations (normal pregnancy serum Ang-2 concentrations) of the normally pregnant women markedly increase as compared with the serum Ang-2 concentrations of the nonpregnant women. On the other hand, the serum Ang-2 concentrations of the women suffering from the pregnancy toxemia do not increase, but show extremely lower values as compared with the normal pregnancy serum Ang-2 concentrations. For this reason, it is considered that the presence or absence of the onset of pregnancy toxemia can be determined by measuring a pregnant women's serum Ang-2 concentration and comparing the measured concentration with the normal pregnancy serum Ang-2 concentration (normal level).

Further, according to the above result, the serum Ang-2 concentration and the amount of urinary protein show the significant negative correlation, which suggests that Ang-2 participates in the maintenance of the glomerular filtration barrier during pregnancy.

Further, to judge the future onset risk of pregnancy toxemia, it is considered that the future onset risk of pregnancy toxemia can be judged by measuring the concentration of angiopoietin-2 in serum (body fluid) when clinical data (amount of urinary protein, mean blood pressure, and the like) does not suggest the onset of pregnancy toxemia, and then comparing the measured concentration with the normal pregnancy serum Ang-2 concentration (normal level).

Thus, the present method described in the examples is a method of examining pregnancy toxemia (first present method) intended for pregnant mammals (humans), characterized by measuring the concentration of angiopoietin-2 in the body fluid (serum), and comparing the angiopoietin-2 concentration obtained in the measurement with the normal level (18.9±3.2 ng/ml of the healthy group). Then, the current or future onset of pregnancy toxemia is judged when the angiopoietin-2 concentration obtained by the measurement is lower than the normal level (18.9±3.2 ng/ml of the healthy group. 6 ng/ml or more.) (The serum angiopoietin-2 concentration of the toxemia group is 4.5±0.6 ng/ml.).

Further, the present method described in the examples is a method of detecting the onset of pregnancy toxemia (second present method) intended for the pregnant mammals (humans), comprising: the measurement step of measuring the angiopoietin-2 concentration in the body fluid (serum); the comparison step of comparing the angiopoietin-2 concentration obtained in the measurement step with the normal level (18.9±3.2 ng/ml of the healthy group); and the judgment step of determining the presence or absence of the onset risk of pregnancy toxemia based on the result of the comparison step (judgment step of determining the current or future onset of pregnancy toxemia). Here, the current or future onset of pregnancy toxemia is judged in the judgment step in the case where the angiopoietin-2 concentration obtained in the measurement step is lower (The serum angiopoietin-2 concentration of the toxemia group is 4.5±0.6 ng/ml) than the normal level (18.9±3.2 ng/ml of the healthy group).

Specifically, here, approximately 77% of the pregnant women whose angiopoietin-2 concentration in serum was less than 8 ng/ml contracted the pregnancy toxemia, and approximately 81% of the pregnant women with the concentration less than 6 ng/ml contracted the pregnancy toxemia. Therefore, for example, when the angiopoietin-2 concentration in pregnant woman's serum is measured, it can be judged that a pregnant woman whose angiopoietin-2 concentration in serum is less than 8 ng/ml currently contracts the pregnancy toxemia or has a high risk of contracting the pregnancy toxemia in the future, and it can also be determined that a pregnant woman whose angiopoietin-2 concentration in serum is less than 6 ng/ml currently contracts the pregnancy toxemia or has an extremely high risk of contracting the pregnancy toxemia in the future.

Here, the concentration measurement (measurement step) of angiopoietin-2 in the body fluid (serum) is the measurement step using the ELISA method intended for the mammals (humans) after 20 weeks of pregnancy.

Also, the reagent containing the reagent for measuring the concentration of angiopoietin-2 in the body fluid like the kit used here can be used as a reagent for the detection of pregnancy toxemia.

What is claimed is:

1. A method of determining pregnancy toxemia comprising: measuring a concentration of angiopoietin-2 in a body fluid of a subject pregnant mammal; comparing the concentration of angiopoietin-2 of said pregnant mammal with a concentration of angiopoietin-2 in a body fluid of a pregnant mammal without pregnancy toxemia; and determining that the subject pregnant mammal is at risk of developing pregnancy toxemia when the measured concentration of angiopoietin-2 in the body fluid of the subject pregnant mammal is less than the concentration of angiopoietin-2 in the body fluid of the pregnant mammal without pregnancy toxemia.

2. The method of determining pregnancy toxemia according to claim 1, wherein the body fluid is blood and wherein the concentration of angiopoietin-2 in the blood of the pregnant mammal without pregnancy toxemia is 6 ng/ml.

3. The method of determining pregnancy toxemia according to claim 1, wherein the body fluid is blood.

4. The method of determining pregnancy toxemia according to claim 1, wherein the measurement is made for the mammals after 20 weeks of pregnancy.

5. The method of determining pregnancy toxemia according to claim 1, wherein the measurement is made by the ELISA method.

\* \* \* \* \*